United States Patent [19]

Walters

[11] 4,064,577
[45] Dec. 27, 1977

[54] BEDDING DRAW SHEET

[75] Inventor: Ronald D. Walters, Oklahoma City, Okla.

[73] Assignee: Hygeia Corporation, Oklahoma City, Okla.

[21] Appl. No.: 744,709

[22] Filed: Nov. 24, 1976

Related U.S. Application Data

[63] Continuation of Ser. No. 651,643, Jan. 23, 1976, Pat. No. 4,021,870.

[51] Int. Cl.² .......................... A47G 9/00; A61G 7/06
[52] U.S. Cl. .................................................. 5/334 R
[58] Field of Search .................. 5/334 R, 335, 334 C, 5/354 B, 354 R; 128/296, 287, 284

[56] References Cited

U.S. PATENT DOCUMENTS

| 1,621,149 | 3/1927 | Blissitt | 5/354 |
| 2,614,273 | 10/1952 | Yancosfki | 5/354 B |
| 2,620,494 | 12/1952 | Kay | 5/354 |
| 2,779,035 | 1/1957 | McMurry | 5/334 R X |
| 3,066,321 | 12/1962 | Kintner | 5/334 C X |
| 3,528,421 | 9/1970 | Vaillancourt et al | 128/284 |
| 3,646,624 | 3/1972 | Zipf | 5/334 R |
| 3,761,973 | 10/1973 | Lezenthal | 5/335 |
| 3,765,040 | 10/1973 | Holstein | 5/334 R |

FOREIGN PATENT DOCUMENTS 632,965  10/1963  Belgium .................................. 5/335

Primary Examiner—Paul R. Gilliam
Assistant Examiner—Victor N. Sakran
Attorney, Agent, or Firm—C. Clark Dougherty, Jr.

[57] ABSTRACT

An improved bedding draw sheet comprised of a base sheet formed of a textile material, a panel formed of a textile material having water penetration-resistant characteristics bonded to the base sheet and a water-absorbent pad removably attached to the panel whereby the water-absorbent pad can be removed and laundered without the necessity of laundering the entire draw sheet.

2 Claims, 3 Drawing Figures

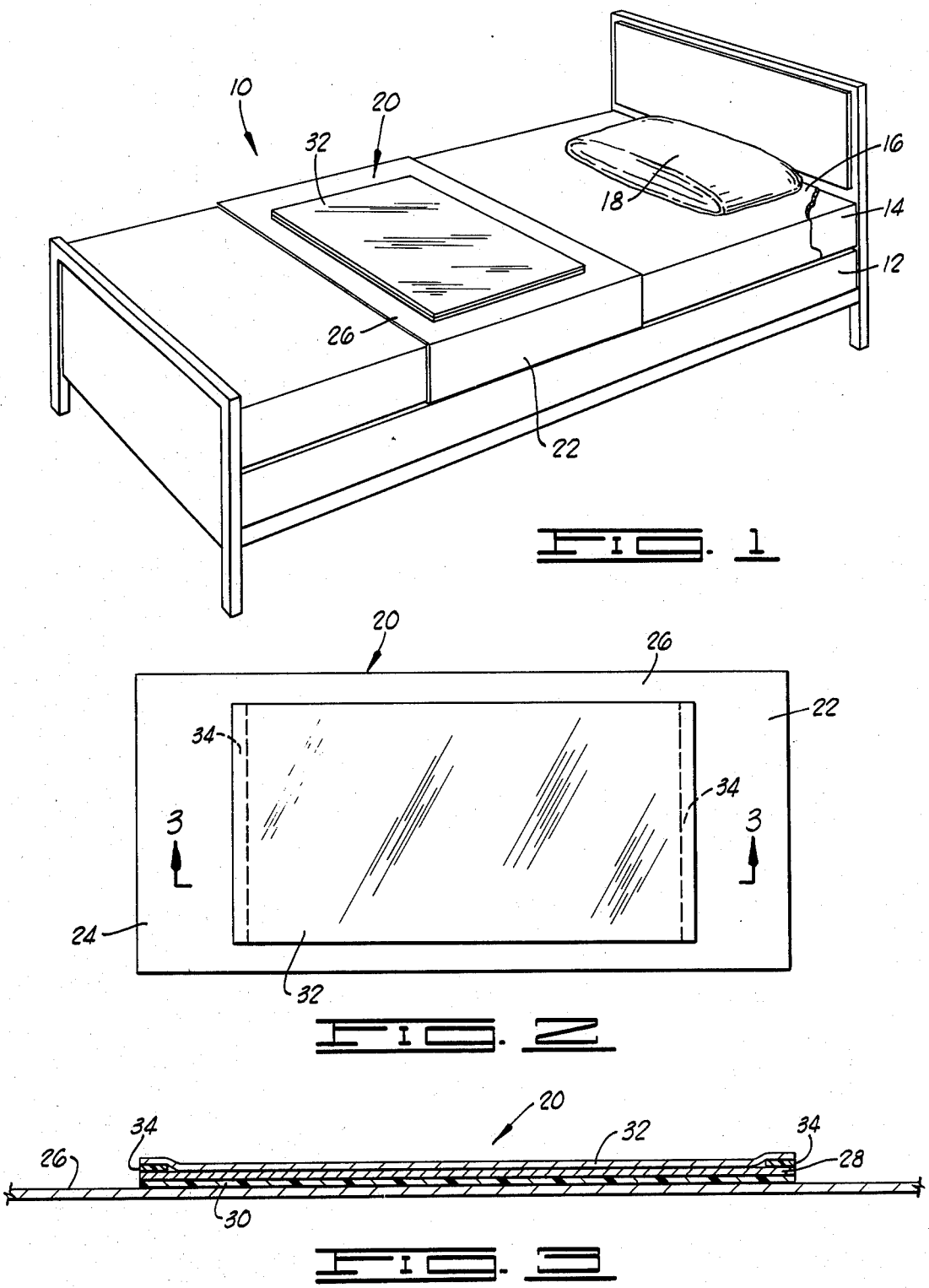

BEDDING DRAW SHEET

This is a continuation of application Ser. No. 651,643, filed Jan. 23, 1976 now Pat. No. 4,021,870.

BACKGROUND OF THE INVENTION

1. Field of the Invention

The present invention relates to an improved draw sheet for bedding, and more particularly, but not by way of limitation, to an improved draw sheet having a removable and launderable water-absorbent pad attached thereto.

2. Description of the Prior Art

Many various combinations of bedding have been utilized in hospitals and the like to prevent water and other fluids deposited on the bedding from penetrating and causing damage to mattresses, etc. For example, rubber, plastic and other waterproof materials in the form of sheets have been utilized over the mattress beneath textile sheets or other bedding materials. While such waterproof sheets successfully prevent water and other fluids from reaching the mattress, they cause considerable discomfort to the person or patient disposed on the bedding due to the poor heat transfer characteristics of such materials. That is, heat and moisture generated by the patient are retained adjacent the patient's body causing considerable discomfort, particularly when such patient is required to remain on the bedding for long periods of time. In addition, the textile sheets and other bedding materials placed on top of such waterproof sheets must be laundered frequently.

Recently, disposable water-absorbent pads have been developed and used which are formed of relatively thick water-absorbent materials and which have a waterproof base formed of a plastic material such as polyethylene. In use, such water-absorbent pads are placed on top of the bedding directly beneath the patient disposed on the bedding whereby the pad can be replaced and disposed of when required without the necessity of changing and laundering textile sheets and other bedding materials utilized on the bed. While the frequent change of such disposable water-absorbent pads can prevent substantial discomfort to the patient, the use of such pads in many cases is ineffective in that they readily become dislodged from beneath the patient or otherwise allow fluids to reach the bedding resulting in the requirement that the bedding be changed. More importantly, the use of such disposable pads involves a considerable expense in that the pads are not reusable.

In addition to the foregoing, a variety of water penetration-resistant draw sheets have been developed and used, some of which have relatively good heat transfer characteristics and thereby abviate patient discomfort, but all of which must be changed and laundered on a frequent basis in order to prevent the accumulation of fluids directly beneath the patient.

By the present invention an improved bedding draw sheet is provided which can be utilized directly beneath a patient on top of other bedding materials, which prevents the penetration of water and other fluids into the bedding materials, which has good heat transfer characteristics, and which includes removable water-absorbent pad portion which can be changed and laundered when required without changing and laundering the entire draw sheet or other bedding materials associated therewith.

SUMMARY OF THE INVENTION

The present invention relates to an improved draw sheet for bedding which comprises a base sheet formed of textile materials, a panel bonded to the base sheet formed of a fine weave textile material having water penetration-resistant characteristics, a water-absorbent pad positioned adjacent the panel and means for removably attaching the water-absorbent pad connected to the pad and the panel.

It is, therefore, a general object of the present invention to provide an improved bedding draw sheet.

A further object of the present invention is the provision of a bedding draw sheet which prevents the penetration of water and other fluids into the bedding material lying beneath the draw sheet, but still has good heat transfer characteristics.

Yet a further object of the present invention is the provision of an improved draw sheet which includes a water-absorbent portion which can be replaced and laundered at frequent intervals without the necessity of changing and laundering the entire draw sheet or other bedding materials associated therewith.

Other and further objects, features and advantages of the invention will be readily apparent from a reading of the description of preferred embodiments which follows when taken in conjunction with the accompanying drawing.

BRIEF DESCRIPTION OF THE DRAWING

FIG. 1 is a perspective view of a bed having the improved draw sheet of the present invention installed thereon.

FIG. 2 is a top view of the improved draw sheet of this invention.

FIG. 3 is a cross-sectional view taken along line 3–3 of FIG. 2.

DESCRIPTION OF PREFERRED EMBODIMENTS

Referring now to the drawing, and particularly to FIG. 1, a bed generally designated by the numeral 10 is illustrated. The bed 10 is comprised of the usual box springs or equivalent means 12 having a mattress 14 disposed thereon. Positioned on top of the mattress 14 is the usual textile sheet 16 upon which a person disposed on the bed lies. As will be understood, any number of other conventional bedding materials, such as mattress covers, etc., can be utilized between the sheet 16 and mattress 14. The customary pillow 18 upon which a person disposed on the bed places his head is shown at one end of the bed 10. The improved draw sheet of the present invention, generally designated by the numeral 20, is positioned on top of the sheet 16 at a point substantially intermediate the ends of the bed 10.

The draw sheet 20 can take a variety of forms, e.g., the form illustrated whereby it covers only an intermediate portion of the sheet 16 and mattress 14, or the draw sheet 20 can be of the same size as the textile sheet 16. In a preferred embodiment, the draw sheet 20 is rectangular in shape having a length such that the end portions 22 and 24 thereof can be disposed around the sides of the mattress 14 and tucked therebeneath, and a width such that when disposed on the bed 10 as illustrated in FIG. 1, the portion of the bed 10 and bedding materials lying beneath the intermediate portion of a patient's body disposed on the bed are covered thereby. As best shown in FIG. 3, the improved draw sheet 20 includes a base portion or sheet 26 which can be formed from any of a variety of conventional launderable textile materials of the type generally utilized for bedding, i.e., textile materials or fabrics which have good heat transfer and comfort characteristics as well as good launderability such as 50% cotton-50% polyester textile materials. A panel 28 formed of a textile material or fabric having water penetration resistance, but still having good heat transfer characteristics and launderability is positioned adjacent and bonded to the top surface of the base sheet 26. While the panel 28 can be of the same shape and size as the base sheet 26, it is preferably of rectangular shape and of reduced size as compared to the base sheet 26. That is, the panel 28 is of a smaller size than the base sheet 26 but of a length and width such that the area of the bed 10 which normally lies beneath the intermediate portion of a patient's body disposed on the bed 10 is covered thereby.

The panel 28 is bonded to the base sheet 26 in a manner such that the base sheet 26 and panel 28 retain their flexibility, launderability and good heat transfer characteristics. This is accomplished in accordance with the present invention by interposing between the base sheet 26 and the panel 28 a thin layer 30 of a binder which upon setting is flexible and adheres to the surfaces of the textile materials 26 and 28 for long periods of time without degradation from the subjection to moisture and high temperatures associated with the laundry of the draw sheet 20. A particularly preferred binder for use in accordance with the present invention is a thermally settable plastic having characteristics such that it is impervious to contact with acid or alkaline fluids and high temperatures. The most preferred such thermalplastic is polyethylene.

As stated above, the panel 28 is preferably formed of a water-resistant textile material having good flexibility and heat transfer characteristics. Suitable such materials are finely woven fabrics formed of cotton and/or synthetic fibers. A particularly suitable fabric which is presently preferred for use in accordance with the present invention is a cotton fabric having a thread count in the range of from about 264 threads per inch to about 280 threads per inch.

Positioned on top of the panel 28 is a pad 32 formed of water-absorbent materials having good comfort and heat transfer characteristics as well as good launderability. Preferably, the pad 32 is formed of a soft commercially available felt material having high water-absorbing properties. While the pad 32 can take a variety of shapes, it is preferably rectangular and of a size corresponding to the panel 28.

The pad 32 is movably attached to the panel 28 so that it is retained over the panel 28 during use of the draw sheet 20. Any of a variety of fastening methods or connector and fastener devices can be utilized so long as the pad 32 remains relatively flat whereby discomfort is not caused a patient lying thereon. Particularly suitable means for removably attaching the pad 32 to the panel 28 comprise a pair of elongated strips of material 34 to which felt adheres stitched or otherwise connected to opposite ends of the panel 28 positioned parallel to the sides of the bed 10. A particularly preferred such adhesive material which withstands repeated laundering, etc., is marketed under the trade name VELCRO and includes a plurality of upwardly extending plastic barbed fingers which readily engage felt and other similar materials.

OPERATION

In operation or use of the improved draw sheet 20 of the present invention, the draw sheet is placed on top of other bedding used on a bed and positioned so that the water-absorbent pad 32 and panel 28 lie beneath the intermediate portion of the patient's body occupying the bed. At intervals when the water-absorbent pad 32 becomes saturated with fluid or otherwise soiled, the pad 32 is detached from the draw sheet 20 and replaced with a fresh, laundered pad. Because the panel 28 beneath the pad 32 resists penetration by water, it is unnecessary to change the entire draw sheet 20 each time the water-absorbent pad 32 is changed. If the pad 32 becomes saturated with fluids prior to changing, and as a result, excess fluids accumulate on the panel 28, such excess fluids can simply be toweled up prior to installing a fresh and dry pad 32 thereon.

The draw sheet 20 has principal utility for use in hospitals and the like where it is subjected to frequent deposits of water and other fluids. In such applications, the water-absorbent pad 32 can be changed frequently and laundered without the necessity of changing the entire draw sheet 20 or any of the other bedding materials utilized therebeneath in a fast, efficient manner. In addition, because the water-absorbent pad 32 as well as the entire draw sheet 20 are launderable, they can be subjected to repeated use over long periods of time while retaining good heat transfer and other health and comfort characteristics.

As will be understood by those skilled in the art, the draw sheet of the present invention and the component parts thereof can take any of a variety of shapes and sizes and various textile materials can be utilized. For example, the panel 28 can be contiguous with the base sheet 26 and/or the base sheet 26 and panel 28 can be formed of the same or different fabrics. Such sizes, shapes and materials will suggest themselves to those skilled in the art upon a reading of the foregoing description of the invention, as will changes in the arrangement of the various components of the invention, which are within the spirit of this invention as defined by the lawful scope of the appended claims.

What is claimed is:

1. An improved draw sheet for bedding which comprises:
   a base sheet formed of textile material;
   a panel bonded to said base sheet formed of a fine weave textile material having a thread count in the range of from about 264 threads per inch to about 280 threads per inch whereby said panel, because of said fine weave has water penetration-resistant characteristics;
   a water-absorbent pad positioned adjacent to said panel; and
   means for removably attaching said water-absorbent pad connected to said water-resistant panel and to said pad.

2. The draw sheet of claim 1 wherein said panel is bonded to said base sheet by means of a thermally-set plastic binder.

* * * * *

UNITED STATES PATENT OFFICE
CERTIFICATE OF CORRECTION

Patent No. 4,064,577  Dated December 27, 1977

Inventor(s) Ronald D. Walters

It is certified that error appears in the above-identified patent and that said Letters Patent are hereby corrected as shown below:

The term of this patent subsequent to May 10, 1994 has been disclaimed.

Signed and Sealed this

*Twenty-first* Day of *February 1978*

[SEAL]

*Attest:*

RUTH C. MASON  LUTRELLE F. PARKER
*Attesting Officer*  *Acting Commissioner of Patents and Trademarks*